United States Patent
Guala et al.

[11] Patent Number: 5,855,230
[45] Date of Patent: Jan. 5, 1999

[54] LUER-LOCK FITTING FOR MEDICAL INFUSION/TRANFUSION LINES

[75] Inventors: Ernesto Guala; Gianni Guala, both of Turin, Italy

[73] Assignee: Industrie Barla Spa, Moncalieri, Italy

[21] Appl. No.: 619,432

[22] Filed: Mar. 21, 1996

[30] Foreign Application Priority Data

Apr. 6, 1995 [IT] Italy .................................. T095U0085

[51] Int. Cl.⁶ ..................................................... F16L 55/10
[52] U.S. Cl. .......................... 138/89; 138/96 T; 604/283; 604/190; 604/905
[58] Field of Search ............................ 138/96 T, 96 R, 138/89, 89.4, 90; 604/283, 190, 905

[56] References Cited

U.S. PATENT DOCUMENTS

| | | | |
|---|---|---|---|
| 4,316,462 | 2/1982 | Baker ..................................... | 604/190 |
| 4,439,188 | 3/1984 | Dennehey et al. .................... | 138/96 R |
| 4,508,367 | 4/1985 | Oreopoulos et al. ................. | 604/283 |
| 4,624,664 | 11/1986 | Peluso et al. . | |
| 5,215,538 | 6/1993 | Larkin ................................... | 604/283 |
| 5,290,253 | 3/1994 | Kira ....................................... | 604/190 |
| 5,624,402 | 4/1997 | Imbert ................................... | 604/283 |

FOREIGN PATENT DOCUMENTS

| | | |
|---|---|---|
| 0 098 411 | 6/1982 | European Pat. Off. . |
| 292 05 787.4 | 4/1995 | Germany . |
| 636 526 | 1/1980 | Switzerland . |
| WO92/07597 | 11/1990 | WIPO . |

Primary Examiner—Denise L. Ferensic
Assistant Examiner—James F. Hook
Attorney, Agent, or Firm—D. Peter Hochberg

[57] ABSTRACT

A Luer-Lock fitting comprising a tubular body having at one end an outer Luer cone connector coaxially surrounded by an innerly threaded attachment cup-like element, and a detachable cap sealingly fitted axially over the Luer cone connector. The cap is formed by a tubular member interposed between the Luer cone connector and the attachment element, which carries a transverse filtering barrier and whose inner end is forcedly coupled onto the outer surface of the Luer cone connector, in proximity of the bottom of the attachment element, so as to define along a substantial portion of the outer surface of the Luer cone connector an annular interspace, opening towards the filtering barrier.

4 Claims, 1 Drawing Sheet

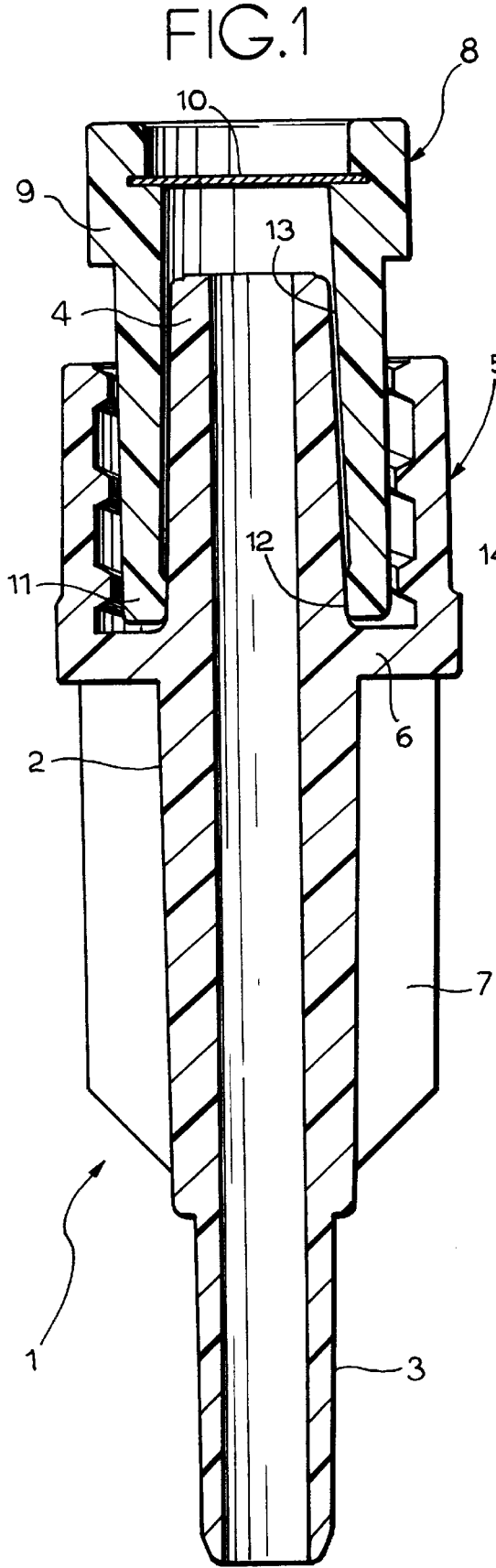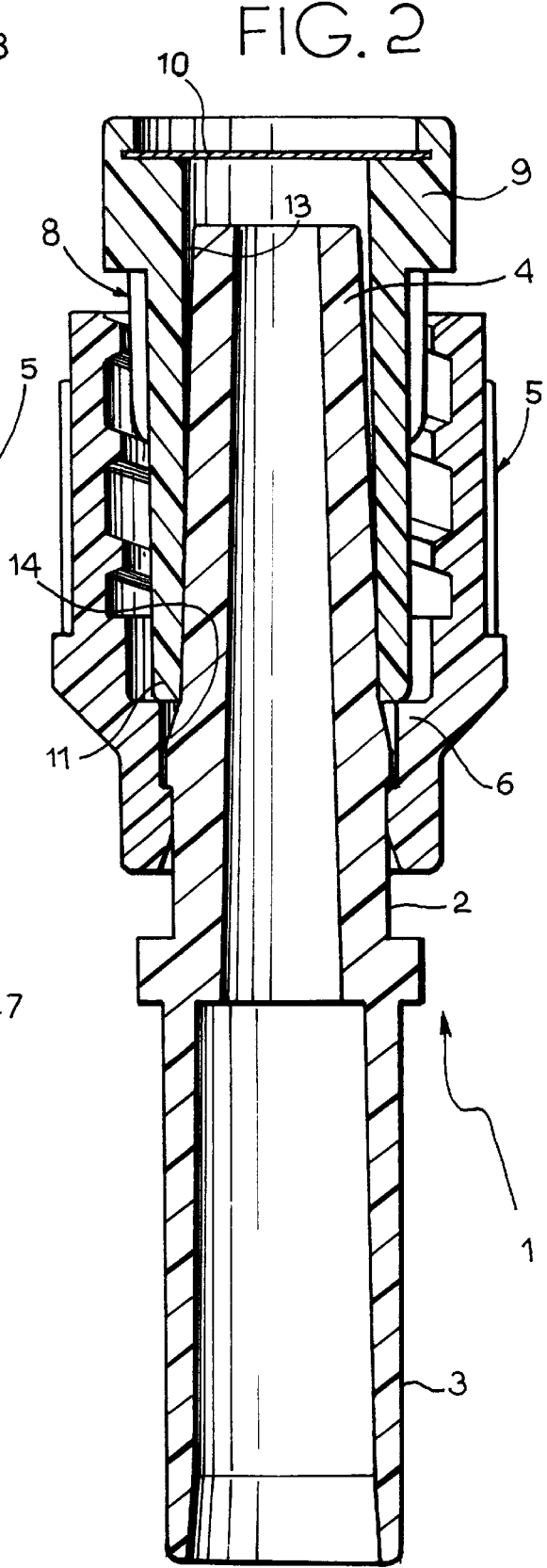

LUER-LOCK FITTING FOR MEDICAL INFUSION/TRANFUSION LINES

The present invention is related to Luer-Lock fittings for medical infusion/transfusion lines, of the type comprising a tubular body having at one end a Luer cone connector coaxially surrounded by a substantially cup-like innerly threaded attachment element, and a detachable cap sealingly connected axially over said Luer cone connector.

A Luer-Lock fitting of the above-referenced type is known from U.S. Pat. No. 4,991,629.

In the Luer Lock fittings of the above referenced type a problem arises in connection with sterilizing the Luer cone connector, namely the outer surface thereof, and with preserving sterilization until the time of use of the fitting. Usually sterilization is performed by introducing a sterilizing gas, for instance ethylene oxide, within the fitting, in such a way that it efficiently leaps also on the outer surface of the Luer cone connector. The cap enables protection of the thus sterilized Luer-cone connector against risks of contamination until the time of use, i.e. when the cap is removed.

The object of the present invention is to provide a Luer-Lock fitting of the type set forth in the above, which allows the sterilizing operation to be carried out in a more convenient and efficient way, enabling the treatment gas to flow over almost the entire outer operative surface of the Luer cone connector, with a simple, functional and cheap construction.

According to the invention, this object is achieved by virtue of the fact that said cap is formed by a tubular element fitted between said outer Luer cone connector and said attachment element and having an outer end projecting beyond said Luer cone connector and carrying innerly a transverse filtering membrane or member, and an inner end forcedly coupled onto the outer surface of said Luer cone connector in proximity of the bottom of said attachment element so as to define, along a substantial portion of said outer surface of the Luer cone connector, an annular interspace, opening towards said filtering membrane.

According to a first embodiment of the invention, said inner end of the cap is formed with an inner annular enlarged portion for the forced coupling onto the outer surface of the Luer cone connector.

According to a variant of the invention, said outer surface of the Luer cone connector is formed with an outer annular enlarged portion for the forced coupling into the inner end of the cap.

The invention will now be disclosed in detail with reference to the accompanying drawings, purely provided by way of non-limiting example, in which:

FIG. 1 is a diagrammatic axially sectioned view of a Luer-Lock fitting for medical infusion/transfusion lines according to a fist embodiment of the invention, and FIG. 2 shows an alternative embodiment of FIG. 1.

Referring initially to FIG. 1, reference numeral 1 generally designates a Luer-Lock fitting for medical infusion/transfusion lines, comprising a unitary body of moulded plastic material 2 defining at one end a first outer Luer cone connector 3, intended to be coupled within the terminal end of a flexible hose, not shown in the drawings, and defining at the other end a second outer Luer cone connector 4.

Reference numeral 5 designates a substantially cup-shaped innerly threaded attachment element, formed integrally with the body 2 and coaxially surrounding a major portion of the outer Luer cone connector 4. The bottom wall of the cup-like attachment element 5, designated as 6, is joined to the Luer cone connector 3 through a number of axial grasp wings 7.

Reference numeral 8 indicates a protection cap sealingly fitted axially over the Luer cone connector 4. The cap 8, which is also made of moulded plastic material, is formed by a tubular member fitted between the Luer cone connector 4 and the attachment element 5 and having an outer enlarged end 9 projecting outwardly beyond the connector 4 and innerly carrying a transverse filtering member 10. The inner end of the tubular cap 8, designated as 11, has an inner annular enlarged portion 12 which is forcedly engaged in correspondence of the root portion of the Luer cone connector 4, i.e. in immediate proximity of the bottom wall 6 of the attachment element 5.

But for the annular enlarged portion 12, the cap 8 has an inner transverse section which is slightly larger than the outer transverse section of the Luer cone connector 4, whereby between the inner surface of the former and the outer surface of the latter an annular interspace 13 is defined, which opens towards the filtering membrane 10. This annular interspace 13 allows efficient sterilization practically of the entire operative outer surface of the Luer cone connector 4, by means of a sterilizing gas supplied within the Luer-Lock fitting 1 through the connector 3.

The variant shown in FIG. 2 is generally similar to the embodiment disclosed in the above, and only the differences will be described in detail, using the same numeral references for identical or similar parts.

Further to a different configuration of the Luer cone connector 3 and of the threaded cup-like element 5, which in this embodiment is constituted by a distinct member rotatably coupled on the body 2, this variant differs from the previously disclosed embodiment in that the forced coupling between the inner end 11 of the tubular cap 8 and the corresponding end of the Luer cone connector 4 is carried out by means of an outer annular enlarged portion 14 of the latter. Also in this case between the inner wall of the cap 8 and the outer surface of the Luer cone connector 4 an annular interspace 13 is defined, which is open towards the filtering barrier 10 so as to allow efficient sterilization of the operative outer surface of the connector 4.

Naturally the details of construction and the embodiments may be widely varied with respect to what has been disclosed and illustrated, without thereby departing from the scope of the present invention such as defined in the appended claims.

What is claimed is:

1. A Luer-Lock fitting for medical infusion/transfusion lines, comprising a tubular body having a Luer cone connector having an outer surface, a substantially cup-like innerly threaded attachment element coaxially surrounding said Luer cone connector and having a bottom wall, and a detachable cap sealingly connected axially over said Luer cone connector, said cap comprising a tubular element fitted between said Luer cone connector and said attachment element and having an outer end projecting beyond said Luer cone connector, wherein said cap is innerly carrying a transverse filtering membrane and has an inner end forcedly coupled onto said outer surface of said Luer cone connector in proximity of said bottom wall of said attachment element so as to define, along a substantial portion of said outer surface of said Luer cone connector, an annular interspace which opens towards said filtering membrane.

2. Luer-Lock fitting according to claim 1, wherein said inner end of said cap has an inner annular enlarged portion for the forced coupling thereof onto said outer surface of said Luer cone connector.

3. Luer-Lock fitting according to claim 1, wherein said outer surface of said Luer cone connector has an outer annular enlarged portion for the forced coupling thereof into said inner end of said cap.

4. A Luer-Lock fitting for medical infusion/transfusion lines comprising:

- a tubular body having a Luer cone connector having an outer surface;
- a substantially cup-like innerly threaded attachment member coaxially surrounding said Luer cone connector; and
- a detachable cap having an outer end projecting beyond said Luer cone connector, said outer end carrying a transverse filter membrane, said detachable cap having a tubular member having an inner surface and an engagement portion which engages a corresponding portion of the outer surface of said Luer cone connector;
- wherein the inner surface of said tubular member is separated from the outer surface of the Luer cone so that all the outer surface of Luer cone connector but the portion therof in contact with the engagement portion of said tubular member is surrounded by an annular interspace opened toward said filter membrane.

* * * * *